United States Patent
Johnson et al.

(10) Patent No.: US 10,363,000 B2
(45) Date of Patent: Jul. 30, 2019

(54) AUTOMATIC REAL-TIME CHANGES TO THE SIZE OF A PATIENTS DATA DISPLAY

(71) Applicant: KONINKLIJKE PHILIPS N.V., Eindhoven (NL)

(72) Inventors: Soren Steiny Johnson, Lynnfield, MA (US); Elizabeth J. Zengo, Newbury, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 282 days.

(21) Appl. No.: 15/103,321

(22) PCT Filed: Dec. 10, 2014

(86) PCT No.: PCT/IB2014/066742
§ 371 (c)(1),
(2) Date: Jun. 10, 2016

(87) PCT Pub. No.: WO2015/087244
PCT Pub. Date: Jun. 18, 2015

(65) Prior Publication Data
US 2018/0153478 A1   Jun. 7, 2018

Related U.S. Application Data

(60) Provisional application No. 61/915,065, filed on Dec. 12, 2013.

(51) Int. Cl.
| | |
|---|---|
| G06T 11/20 | (2006.01) |
| A61B 5/00 | (2006.01) |
| A61B 5/044 | (2006.01) |
| A61B 5/0205 | (2006.01) |
| A61B 5/145 | (2006.01) |
| G06F 3/0481 | (2013.01) |
| A61B 5/01 | (2006.01) |

(52) U.S. Cl.
CPC ........... *A61B 5/743* (2013.01); *A61B 5/0205* (2013.01); *A61B 5/044* (2013.01); *A61B 5/14542* (2013.01); *A61B 5/742* (2013.01); *A61B 5/7445* (2013.01); *A61B 5/01* (2013.01); *G06F 3/0481* (2013.01)

(58) Field of Classification Search
CPC ..... G16H 40/63; G16H 10/60; G06F 19/3418
See application file for complete search history.

(56) References Cited

U.S. PATENT DOCUMENTS

| | | |
|---|---|---|
| 5,473,536 A | 12/1995 | Wimmer |
| 2005/0229110 A1 | 10/2005 | Gegner |

(Continued)

FOREIGN PATENT DOCUMENTS

| | | |
|---|---|---|
| WO | 2012/085762 | 6/2012 |
| WO | 2012/158720 | 11/2012 |

*Primary Examiner* — Nan-Ying Yang

(57) ABSTRACT

A medical monitoring system includes one or more electronic processors and one or more display devices. The one or more electronic processors are configured to receive vital signs of each a plurality of patients and dynamically configure in real-time a display of the received vital signs which includes for each patient an individually assigned patient sector display sized from available space for the display based on a priority order. The one or more display devices display the configured display of the plurality of patient sector displays.

13 Claims, 4 Drawing Sheets

(56) References Cited

U.S. PATENT DOCUMENTS

| | | |
|---|---|---|
| 2009/0054735 A1 | 2/2009 | Higgins |
| 2009/0275846 A1* | 11/2009 | Costa Ribalta ....... G06F 19/321 600/509 |
| 2012/0095778 A1 | 4/2012 | Gross |
| 2013/0044111 A1* | 2/2013 | VanGilder .............. A61B 5/044 345/440 |

* cited by examiner

AUTOMATIC REAL-TIME CHANGES TO THE SIZE OF A PATIENTS DATA DISPLAY

CROSS REFERENCE TO RELATED APPLICATIONS

This application is the U.S. National Phase application under 35 U.S.C. § 371 of International Application No. PCT/IB2014/066742, filed Dec. 10, 2014, published as WO 2015/087244 on Jun. 18, 2015, which claims the benefit of U.S. Provisional Patent Application No. 61/915,065 filed Jul. 5, 2013. These applications are hereby incorporated by reference herein.

The following relates generally to medical monitoring of patients. It finds particular application in conjunction with patient monitor displays, and will be described with particular reference thereto. However, it will be understood that it also finds application in other usage scenarios and is not necessarily limited to the aforementioned application.

Central monitoring of patients in a healthcare environment typically occurs in a healthcare treatment center such as a hospital ward, emergency department and the like. Many patients are monitored simultaneously by physiological sensors which transmit measurements of vital signs to a central monitoring system. Vital signs can include various measures of body temperature, heart rate, blood pressure, respiratory rate, and the like. The transmitted measures are received and display typically in a waveform and/or a numeric format. The vital signs for the group of patients being monitored are typically displayed on a common display, which provides an overview of the current status of each patient to healthcare practitioners involved in the treatment facility. Vital signs can be sourced which means a set of vital signs are associated with a selected patient. Sourced vital signs can be transmitted or not. For example, a patient may accidentally disconnect a sensor which interrupts transmission. The sensor or vital sign associated with the sensor is still sourced and to be displayed, but no data is transmitted. This can indicate an alarm or alert condition.

The display of the patient group is often organized by physical location such as by bed location. The display includes for each patient a sector or display space. The patient sector typically includes a header space which identifies the patient and/or location, and any alarm conditions. The patient sector includes the waveforms of vital signs and alphanumeric measures for the patient. For example, an ECG waveform is displayed with a numeric value of the current heart rate, and a plethysmograph waveform is displayed with a $SpO_2$ numeric value. Additional numeric values can be reported in space adjacent to waveforms such as respiration rate, non-invasive blood pressure (NBP), etc. The display of the patient group is typically organized into columns of the patient sectors.

Displays can include up to 16 patient sectors on a single display or up to 32 patient sectors on a dual display. Displays are strategically placed in the treatment facility to communicate the state of each patient quickly to the healthcare practitioners such as doctors, nurses, aides, etc. Displays are often located in and around nursing stations, central locations, or locations frequency passed by the healthcare practitioners. The number of displays is often limited due to cost, and/or available physical space to place the displays. Moreover, expanding the number of displays can reduce the effectiveness by increasing the time to locate information about patients, or causing a healthcare practitioner to interrupt a task or change focus to assess the situation.

The displays are organized for fast visual comprehension with a consistent organization. For example, the location of patients on the display is consistent. The organization within a patient sector is consistently organized such as header information at the top of the sector, waveforms on the left side of the sector in a list format, and numeric data on the right of each waveform. However, some patients are more acute than others and monitoring needs vary. Although the treatment facility may have a baseline of certain waveforms to be monitored for every patient, other waveforms may be helpful for certain patients. Furthermore, acuity level for a patient can change over time and therefore monitoring needs for each patient may change over time.

One basic approach is to assign a fixed sector space to each patient. Patient sectors are typically placed within a single columnar display or a multi-columnar overall display. A fixed sector space can be quite large to accommodate different patient needs and limited by the addition of more overall display space. A modified approach is dividing the space differently between columns of patient sectors. For example, a first column is divided into 4 patient sectors, while a second column is divided into 2 patient sectors. The modified approach creates problems with the overall order of patients and does not completely address variability between patients, does not address variability in acuity level of an individual patient, and typically means moving the location of the sector from one column to another to increase the size.

Another approach is to ask the healthcare practitioner to assign space to different patient sectors. This is typically accomplished with the healthcare practitioner interacting with the system, often with a password protected secure layout, and manual adjustment of the size. One modified approach to reduce the time required to optimize space is a minimize function which leaves only the patient header visible. Another approach includes the use of paging of the display. However, the interaction of the healthcare practitioner with the system to either fixed the format, minimize individual sectors, or page the display interrupts patient care tasks and/or diverts attention away from patient care. For example, in a team approach, designating who makes the modification, how the modification is made, and when interrupts the information flow to the healthcare provider team. System interactions by more than one member means a healthcare practitioner stopping to interact with the system versus obtaining visual information while providing patient care or moving from one location to another preparing for the next patient interaction. None of these approaches involve the current patient needs, but rather focus on the form of the information delivery.

The following discloses a new and improved method and system for automatic real-time changes to the size of a patient's data display which addresses the above referenced issues, and others.

In accordance with one aspect, a medical monitoring system includes one or more electronic processors and one or more display devices. The one or more electronic processors are configured to receive vital signs of each a plurality of patients and dynamically configure in real-time a display of the received vital signs which includes for each patient an individually assigned patient sector display sized from available space for the display based on a priority order. The one or more display devices displays the configured display of the plurality of patient sector displays.

In accordance with another aspect, a method of patient monitoring includes receiving vital signs of each of a plurality of patients and dynamically configuring in real-time a display of the received vital signs which includes for each patient an individually assigned patient sector display size from available space for the display based on a priority order. The configured display of the plurality of patient sector displays is displayed.

In accordance with another aspect, a medical monitoring system includes a module configured to source vital signs of each of a plurality of patients and a module configured to assign available space from a display to a variably sized display sector for each patient, each sector individually assigned space sized according to a priority order and to include a patient identification space and graphical illustrations of one or more vital signs of the sourced vital signs for the patient. The system further includes a module configured to dynamically change in real-time the assigned sector size and the display of vital signs in each of the patient sectors according to changes in the vital signs of the plurality of patients and one or more display devices which display the configured display of the plurality of patients.

One advantage is a dynamically variable sized patient sector.

Another advantage resides in dynamically changing the patient sector as the patient acuity changes.

Another advantage resides in accommodating different monitoring needs among individual patients in a monitored patient group.

Another advantage resides in eliminating competing healthcare practitioner interactions to make changes in display configurations.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 diagrammatically illustrates an embodiment of the automatic real-time changes to the size of a patient's data display system in an exemplary treatment facility with an exemplary partial patient monitoring display in an exploded view.

Figure 4:
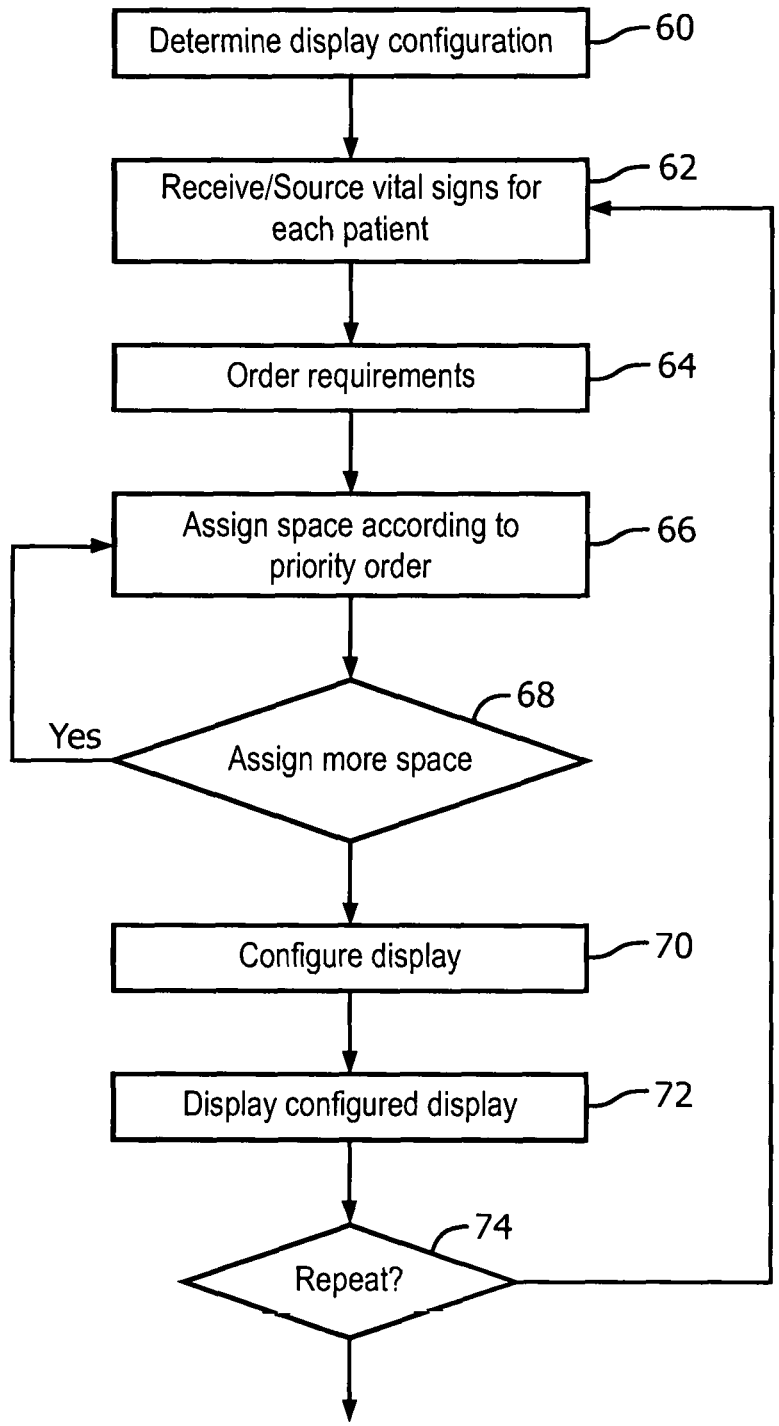

FIG. 4 flowcharts one method of automatic real-time changes to the size of a patient's data display.

Figure 1:
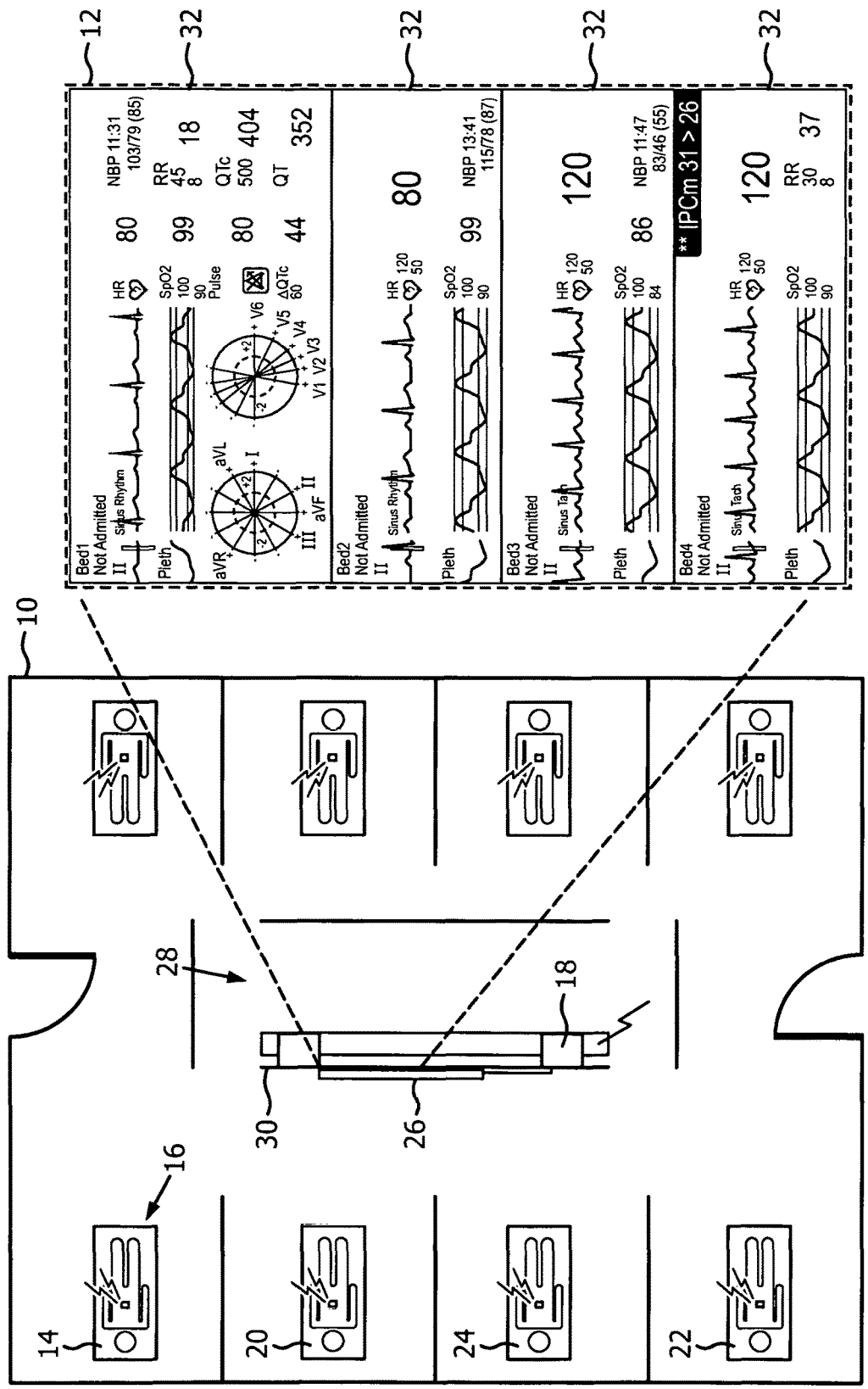

With reference to FIG. 1, an embodiment of the dynamic change to patient data display system in an exemplary treatment facility 10 with an exemplary partial patient monitoring display 12 in an exploded view is diagrammatically illustrated. The treatment facility is shown as one physical location, but can include geographically distributed patients. The treatment facility monitors multiple patients 14. Each patient can have one or more monitoring devices 16 or sensors which sense physiological activity and transmit measurements of the physiological activity or vital sign to a computer device 18. The sensing device can transmit over a network which is wireless, wired, or a combination. The sensing device can sense one or more measures of patient vital signs. The sensing devices can be the same or different between patients. For example, a first sensing device of a first patient 20 senses and transmits $SpO_2$ measures, a second device of a second patient 22 senses and transmits $SpO_2$ and ECG measures, and a third device of a third patient 24 senses and transmits $SpO_2$, ECG, and ST segment measures. The sensing devices can process the measures and transmit values or waveforms, or transmit raw data with further processing of measures into graphical illustrations or waveforms performed by the computer device 18.

The computer device 18, which includes one or more electronic processors, is programmed to receive vital signs of a plurality of patients and dynamically configure in real-time the display 12 of the received vital signs on a display device 26. The computer device 18 can be programmed further to source the individual sensing devices and/or vital signs of the patients, e.g. associate a set of vital signs with a patient, verify operational status, and the like. The display device can be visibly positioned to healthcare practitioners such as at a nursing station 28, mounted on a central wall 30, and the like. In other embodiments, the display device is included in the computing devices of individual healthcare practitioners. The display 12 includes a plurality of patient display sectors, and for each patient an individually assigned patient sector 32 display sized from available space for the display based on a priority order.

The computer device assigns available space determined from the height of a column, e.g. number of pixels, of the display device incrementally to each variably sized patient display sector. Available space is assigned to each sector individually. Available space is assigned in a priority order. Each sector is sized individually to include a patient header space and graphical illustrations of one or more vital signs of the vital signs for the patient.

The priority order is based on a set of rules. The set of rules can include the assignment of unassigned space, first to sectors with a user-specified minimum size, second to sectors with one or more user-specified data elements, third to sectors smaller than a predetermined minimum sector size, fourth to smaller sectors, fifth to sectors with space assigned to all sourced vital signs, sixth to sectors with a user-specified maximum sector size with the maximum size assigned, and seventh to sectors with no sourced vital signs. For example, each sector is initially assigned a height or size. Sectors can be organized based on the rules into a heap data structure ordered according to the rules. The sector at the top of the heap data structure is assigned space in increments of a graphical illustration of a vital sign or waveform. Header space for each patient sector can be initially assigned or alternatively header space included in the initial assignment of vital sign space. After the assignment to the sector, the heap data structure is resorted and the process repeated until all unassigned space is assigned to sectors in the column.

The rules can limit sector size to a predetermined minimum sector size based on site specific policies, such as a minimum number of vital signs or ideal sector size targets. The rule with smaller sectors spreads the available space over sectors less than others for an even distribution. Rule ties of sectors can be broken with favor to those sectors of patients with more vital signs transmitted or sourced. In other embodiments, sector sizes can favor patients based on a number of graphical illustrations or waveforms, number of numerics, a patient acuity such as derived from an Early Warning Score (EWS), or a combination.

The computer device dynamically configures in real-time the display of vital signs in each of the patient sectors according to the assigned space. The assigned space for a sector includes header space and vital sign space. Header information is placed in the header space of the sector and vital sign information for one or more vital signs is placed in the vital sign space of the sector. The rules can further control which vital signs are displayed in each sector based on sector size.

The display device 26 displays the configured display of the plurality of patients. The configured display includes the columns of the patient sector displays configured by the computer device. The display is updated or refreshed in real-time by the computer device as vital signs are received, and re-displayed by the display device.

The computer device 18 can be a computer configured to receive the transmitted and/or sourced vital signs and connected to the display device 26. The computer device 18 can be connected to and participate in a network. The computer device includes one or more electronic processor or electronic processing device, one or more display devices which displays the monitored vital signs, menus, panels, and user controls, and can include at least one input device which inputs the healthcare practitioner selections, such as site preferences. The computer device can be a desktop computer, a laptop, a tablet, a mobile computing device, a smartphone, and the like. The computer device can include a network-based server computer. The disclosed space assigned and display configuration techniques are suitably implemented using a non-transitory storage medium storing instructions (e.g., software) readable by an electronic data processing device and executable by the electronic data processing device.

The display device 26 as used herein encompasses an output device or a user interface adapted for displaying images and/or data. The display device can include a single display or dual display. Examples of the display device include a computer monitor, a television screen, a touch screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display, and the like.

Figure 2:
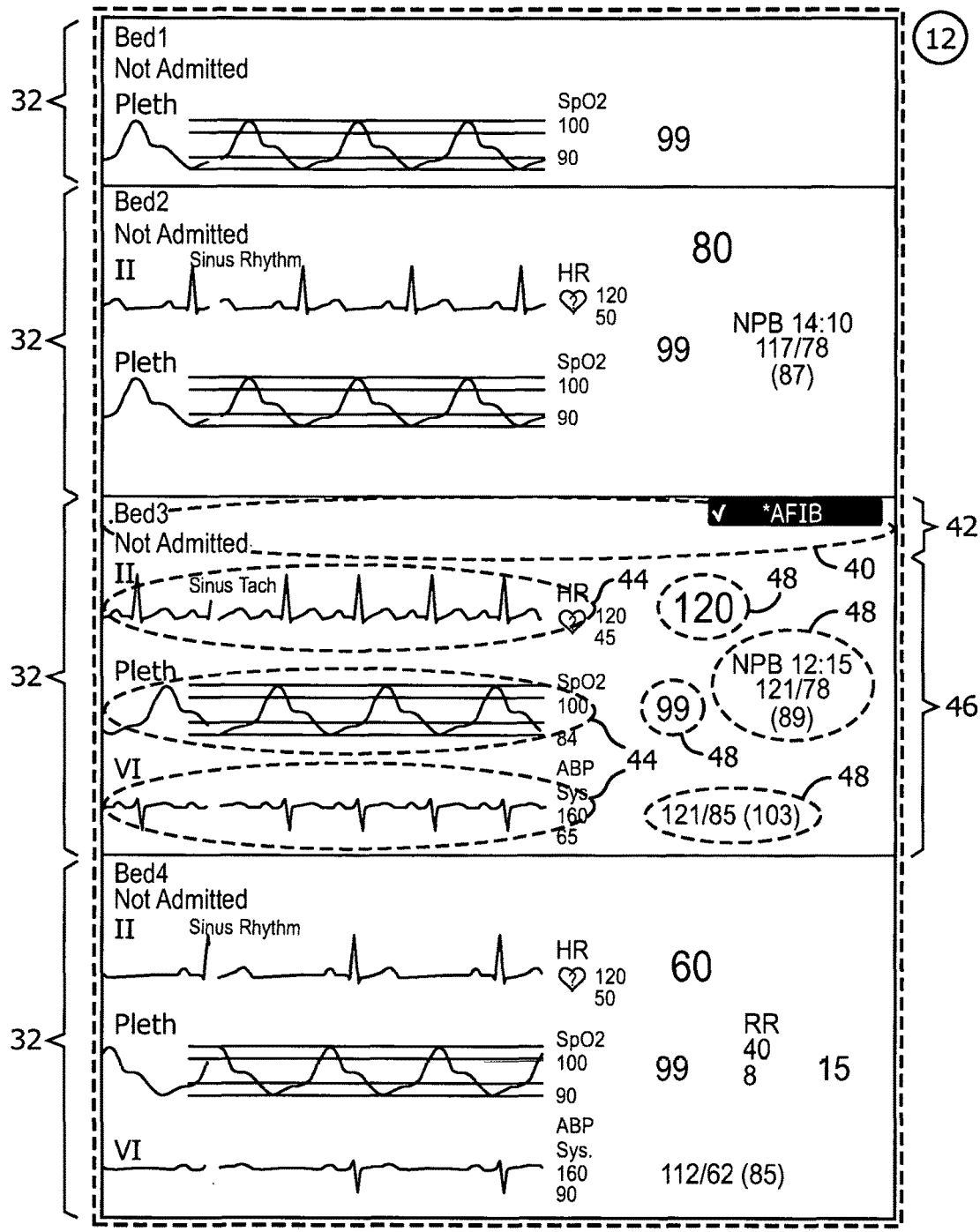
FIG. 2 illustrates an exemplary of a display with dynamically changed variable sized patient sectors.

With reference to FIG. 2, an exemplary of a display 12 with dynamically changed variably sized patient sectors 32 is illustrated. Header information 40 is configured or placed in the header space 42 such as a bed location, a scoring indicator of an acuity score, such as the EWS, set alarm conditions, and the like. Graphical illustrations of the vital signs 44, such as waveforms are configured or placed in the variable sized vital sign space 46.

Each vital sign includes at least one measurement of patient temperature, patient heart rate, patient blood pressure, or patient respiratory rate. A graphical illustration of each vital sign can include one or more measures. Each graphical illustration of a vital sign or waveform can be accompanied by one or more numerics 48. The numeric can be a function of the measures displayed in the waveform or include independent measures.

Display space is assigned to sectors based on a minimum height of the graphical illustration of the vital sign. The vital sign can include a range of heights. For example, waveforms can be preferably displayed with a height of 100 pixels, but can be displayed with a minimum height of 80 pixels. Space for one waveform is assigned in one increment of 80 pixels or an increment of 100 pixels, but can be adjusted or resized to 80 pixels to fit within a sector. Space can be assigned based on neat sizes to provide a uniform appearance. Exceptions to neat sizes such as an ST Map can be assigned with different incremental or minimum sizes.

In one embodiment, the order of the assignment of space for waveforms can be ordered. For example, with a first waveform with a first priority and a second waveform with a second priority, the assignment assigns space corresponding to the range of the first waveform before assigning space for the second waveform. Other embodiments include allowing selection of the second waveform before the first waveform if sufficient space is not available for the first waveform and the first waveform is larger than the second waveform.

Figure 3:
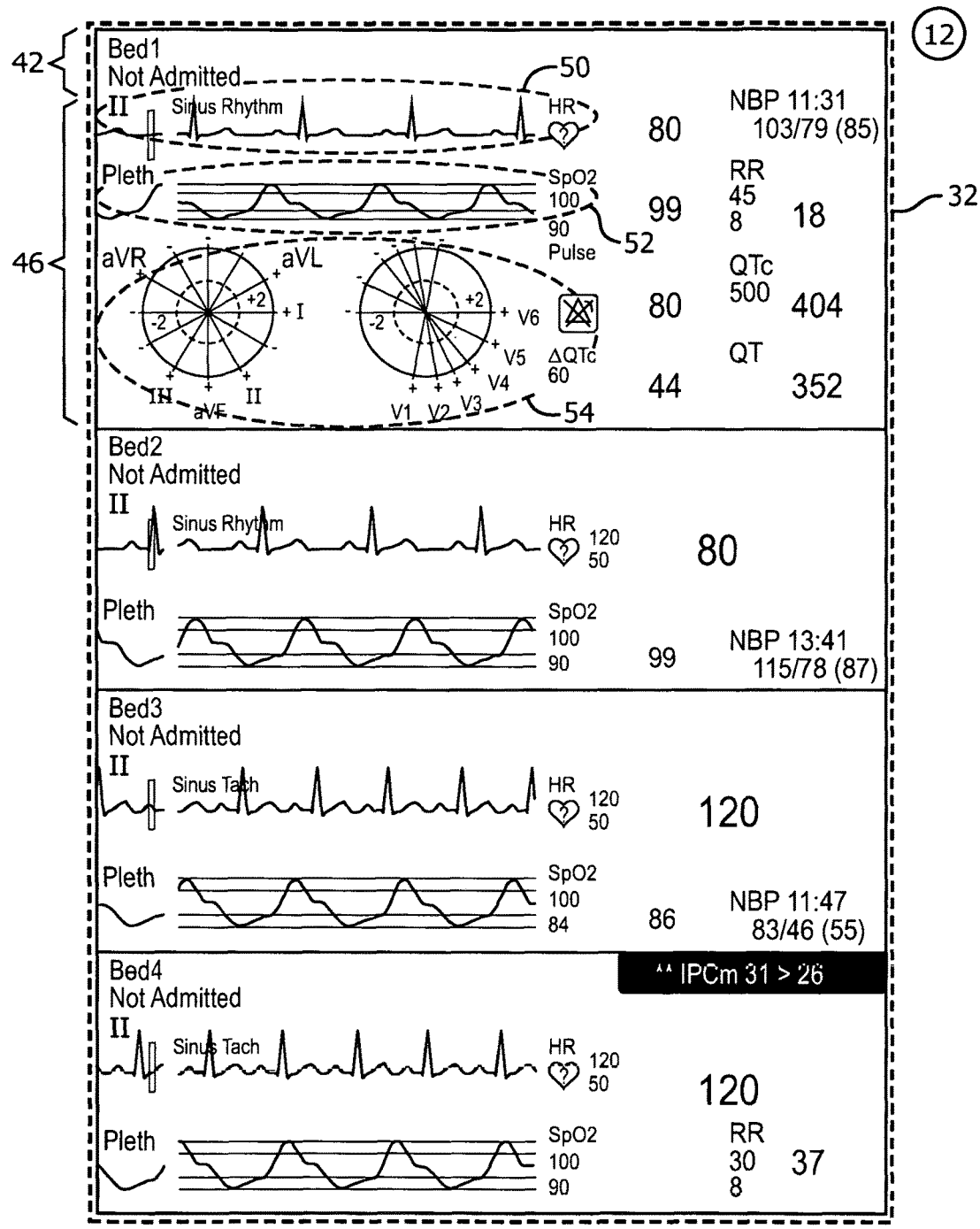
FIG. 3 illustrates another exemplary of a display with dynamically changed variable sized patient sectors including a patient sector with differently sized vital sign displays.

Space can be dynamically reassigned based on changes in acuity, changes in the monitored vital signs, or additional sourced vital signs or removed sourced vital signs. As more vital signs are transmitted and/or sourced for a patient, the added vital signs indicate a change in patient acuity and the computer device receives and configures the display with the added vital sign. As a vital sign is removed, e.g. no longer sourced, the computer device removes the vital sign from the patient sector and re-orders the assignment of space during a refresh accordingly. Small adjustments in space can be performed by the computer device based on the ranges of vital sign waveforms and remaining space. For example, with space assigned in a column to sectors and a remainder to 10 pixels, the remaining 10 pixels can be used to resize waveforms with the range of the waveform, expand header space, expand space between waveforms in a sector, and the like. The assignment of remaining space can provide a more uniform consistent appearance With reference to FIG. 3 another exemplary of a columnar display with dynamically changed variable sized patient sectors 32 including a patient sector with differently sized vital sign displays is illustrated. Three graphically illustrated vital signs are shown 50, 52, 54. One vital sign graphically illustrated includes a ST map 54 or multi-axis portrait of one patient's ST segment values and trends derived from vertical (limb leads) and horizontal (chest leads) planes. The individual minimum height ranges or space size for each graphically illustrated vital sign can vary within a sector. The size of each sector can vary with the number and type of vital signs configured for display.

With reference to FIG. 4 one method of dynamically changing patient data displays is flowcharted. In a step or module 60, the display configuration requirements are determined. The number of columns of display, and the number of displays are determined. For example, the display can include a display for a single display or for a dual display device. The configuration requirements include the amount of available space to be assigned or unassigned space, e.g., number of pixels in a column of sectors.

The vital signs for a plurality of patients are received in a step or module 62. The step can include sourcing of the vital signs, removing of sources, and/or adding vital signs for each patient. In a step or module 64, ordering requirements are determined for each patient display sector. The step can include receiving user specified minimum sizes, user specified data element, changes to the predetermined minimum sector sizes, user specified maximum sector sizes, EWS, other measures of patient acuity, etc. For example, attributes of the sectors with user-specified data elements are identified and updated. Sectors attributes are updated for each sector according to the rules which determine the priority order.

In a step or module 66, space is assigned to the individual patient sectors from the unassigned space based on the priority order by the computer device. The step can include ordering the priority based on a set of rules. The rules can include assigning unassigned space first to sectors with a user-specified minimum size, second to sectors with one or more user-specified data elements, third to sectors less than a predetermined minimum sector size, fourth to smaller sectors, fifth to sectors with space assigned to all sourced vital signs, sixth to sectors with a user-specified maximum sector size and the maximum size assigned, and seventh to sectors with no sourced vital signs. The step can include constructing and/or modifying the heap data structure to identify the priority order of sectors for space assignment. The step can include priorities of vital sign displays by patient sector. For example, ECG and $SpO_2$ waveforms are assigned prior to assigning space for other waveforms or graphical illustrations of vital signs. The step can include assigning space to sectors based on a minimum height of the graphical illustration of the vital sign included in the assigned sector. The step can include assigning space for header space and vital sign space in each patient display sector. The step can include variable sizes for vital signs included individual patient sectors.

In a decision step or module 68, the assignment of space continues iteratively until the unassigned space is assigned. The iterative process dynamically configures in real-time for each patient an individually assigned patient sector display sized from available space for the display based on a priority order.

The display is configured in real-time based on the assigned space to each sector in a step or module 70. The step includes placing header information in the header space of each sector and vital sign information in the variably spaced vital sign space of each sector. The vital sign information for each sector can vary with the number and type of vital signs. For example, one patient can include a multi-axis portrait (ST map) of the patient's ST segment values and trends derived from vertical (limb leads) and horizontal (chest leads) planes in addition to other vital signs displayed. The display of vital signs includes graphical illustrations for individual vital signs. Each graphical illustration of one vital sign includes a minimum height size. The individual vital sign information is updated in real-time as vital signs are received from the monitoring devices or sensors, e.g. updated waveforms and numerics. In a step or module 72, the configured display of the plurality of patients is displayed on the display device or devices.

In a decision step or module 74, the process can be repeated. For example, as indications or notices of an additional vital sign are received or sourced, the process can be repeated which dynamically adjusts the display of the displayed vital signs with the additional sourced or received vital sign. In another example, as monitoring devices are disconnected, the vital signs are no longer sourced and the process repeats to dynamically remove the no longer sourced vital sign. The steps can be performed with a non-transitory computer-readable storage medium carrying software which controls one or more electronic data processing devices to perform the steps.

In one exemplary embodiment, the acuity of each patient assigned to a column of sectors is determined. The rules are applied to the relative acuities to assign a relative height to each sector. The rules are applied to the relative height of each sector to assign which monitored vital signs are displayed. In assigning the relative height, the rules take into account minimum display heights, e.g. allocate relative height in increments of the minimum display height such that the sectors are not assigned heights which leave unusable space, due to the minimum height rules, in a plurality of the sectors.

The monitored vital signs, including those that are not currently displayed are monitored to dynamically determined changes in the relative acuity, e.g. changes in the EWS. When the relative acuity changes the height of each sector is automatically reassessed and reallocated. Changes in allocated space automatically reassess and can change the display vital signs. Thus, when the acuity of one patient improves, some of the improved patient's sectors space can be reassigned to the sector space of one or more other patients. Similarly when a patient's acuity deteriorates, the rules can reallocate sector space and give the deteriorating patient more sector space. The rules of determining which vital signs are displayed in each sector may be based in part on the acuity score. For example, unstable vital signs can be given preference over stable or closer to normal vital signs.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:
1. A medical monitoring system comprising:
one or more electronic processors configured to:
receive vital signs of each of a plurality of patients; and
dynamically configure in real-time a display of the received vital signs which includes for each patient an individually assigned patient sector display sized from available space for the display based on a priority order; and one or more display devices which display the configured display of the plurality of patient sector displays;

wherein the priority order is based on a set of rules, the set of rules including the assignment of space to sectors based on specified minimum size, specified data elements, space assigned to all sourced vital signs, a specified maximum sector size, and an absence of sourced vital signs, the set of rules including the assignment of space:

first to sectors with a user-specified minimum size,
second to sectors with one or more user-specified data elements,
third to sectors smaller than a predetermined minimum sector size,
fourth to smaller sectors,
fifth to sectors with space assigned to all sourced vital signs,
sixth to sectors with a user-specified maximum sector size with the maximum size assigned, and
seventh to sectors with no sourced vital signs.

2. The system according to claim claim 1, wherein sector display sizes are dynamically reassigned based on changes in monitored vital signs of at least one patient.

3. The system according to claim 1, wherein the display of vital signs includes a graphical illustration for each vital sign and space is assigned to sectors based on a minimum height of the graphical illustration of the vital sign included in the assigned sector.

4. The system according to claim 1, wherein the assigned space of each patient sector display includes a header space and a variable sized vital sign space for graphical illustrations of one or more vital signs, each graphical illustration of one vital sign including a minimum height size, the vital sign space sized in increments of the minimum height sizes.

5. The system according to claim 1, wherein space is dynamically reassigned based on additional sourced vital signs or removed sourced vital signs of at least one patient.

6. The system according to claim 1, wherein at least one vital sign for at least one patient includes a multi-axis portrait (ST map) of one patient's ST segment values and trends derived from vertical (limb leads) and horizontal (chest leads) planes.

7. A method of patient monitoring, comprising:
receiving vital signs of each of a plurality of patients;
dynamically configuring in real-time a display of the received vital signs which includes for each patient an individually assigned patient sector display size from available space for the display based on a priority order, the priority order based on a set of rules, the set of rules including:
assigning unassigned space first to sectors with a user-specified minimum size,
assigning unassigned space second to sectors with one or more user-specified data elements,
assigning unassigned space third to sectors less than a predetermined minimum sector size,
assigning unassigned space fourth to smaller sectors,
assigning unassigned space fifth to sectors with space assigned to all sourced vital signs,
assigning unassigned space sixth to sectors with a user-specified maximum sector size and the maximum size assigned,
assigning unassigned space seventh to sectors with no sourced vital signs; and
displaying the configured display of the plurality of patient sector displays.

8. The method according to claim 7, further including:
dynamically reassigning sector display sizes based on changes in monitored vital signs of at least one patient.

9. The method according to claim 7, wherein the display of vital signs includes a graphical illustration for each vital sign and space is assigned to sectors based on a minimum height of the graphical illustration of the vital sign included in the assigned sector.

10. The method according to claim 7, wherein the assigned space of each patient sector display includes a header space and a variable sized vital sign space for graphical illustrations of one or more vital signs, each graphical illustration of one vital sign including a minimum height size.

11. A non-transitory computer-readable storage medium carrying software which controls one or more electronic data processing devices to perform the method according to claim 7.

12. An electronic data processing device configured to perform the method according to claim 7.

13. A medical monitoring system, comprising:
one or more electronic processors configured to:
receive vital signs of each of a plurality of patients; and
dynamically configure in real-time a display of the received vital signs for each patient in an individually assigned patient sector display, the individual patient sector display being dynamically sized from available space for the display based on a priority order, the priority order being based on a set of rules, the set of rules assigning space to sectors, the rules assigning space in the following order:
first, based on specified minimum size,
after the specified minimum size, based on specified data elements,
after the specified data elements, based on space assigned to all sourced vital signs,
after space assigned to all sourced vital signs, based on a specified maximum sector size, and
after the specified minimum vector size, based on an absence of sourced vital signs; and
one or more display devices configured to display the plurality of patient sector displays concurrently on a common display screen.

\* \* \* \* \*